United States Patent [19]

Gordon et al.

[11] Patent Number: 4,507,111

[45] Date of Patent: Mar. 26, 1985

[54] SURGICAL SCRUB

[75] Inventors: Marvin Gordon, East Windsor; Joseph Lichtenstein, Colonia, both of N.J.

[73] Assignee: Whitman Medical Corporation, Clark, N.J.

[21] Appl. No.: 435,335

[22] Filed: Oct. 19, 1982

Related U.S. Application Data

[63] Continuation-in-part of Ser. No. 241,486, Mar. 9, 1981, abandoned, and a continuation-in-part of Ser. No. 298,246, Aug. 31, 1981, Pat. No. 4,415,288.

[51] Int. Cl.³ ............................................. A61M 35/00
[52] U.S. Cl. ......................................... 604/3; 401/134
[58] Field of Search ................... 604/3; 401/132, 133, 401/134, 135

[56] References Cited

U.S. PATENT DOCUMENTS

| | | | |
|---|---|---|---|
| 2,229,749 | 1/1941 | Little | 401/135 |
| 3,324,855 | 6/1967 | Heimlich | 128/269 |
| 3,724,962 | 4/1973 | Herrning | 401/134 X |
| 3,922,099 | 11/1975 | Christine et al. | 401/134 |

Primary Examiner—Edward M. Coven
Attorney, Agent, or Firm—Holman & Stern

[57] ABSTRACT

A surgical scrub apparatus includes a liquid-containing rupturable cylindrical cartridge which is slidable within a tubular handle having two (2) hollow interior spikes projecting longitudinally from one end. The cartridge can be inserted sufficiently far to cause rupture of the cartridge by both spikes. Liquid from the ruptured cartridge flows through the hollow spikes to an applicator sponge having two (2) wide area applicator surfaces. The hollow spikes are oriented such that one is always disposed higher than the other when the applicator surfaces of the sponge are disposed substantially horizontally. The upper spike can be disposed at a position wherein the liquid pressure applied thereto is less than ambient such that the upper spike serves as a vent passage which admits air into the cartridge. The lower spike thereby serves primarily as an outflow for liquid from the cartridge and air replaces the egressing liquid through the upper spike. The forward ends of the spikes are truncated on respective bias planes which diverge in the direction toward the remote end of the handle. The spikes are transversely spaced as far as possible to maximize the liquid pressure difference at the punctures made in the cartridge by the spikes when the handle is oriented with the sponge tilted slightly downward from horizontal.

16 Claims, 12 Drawing Figures

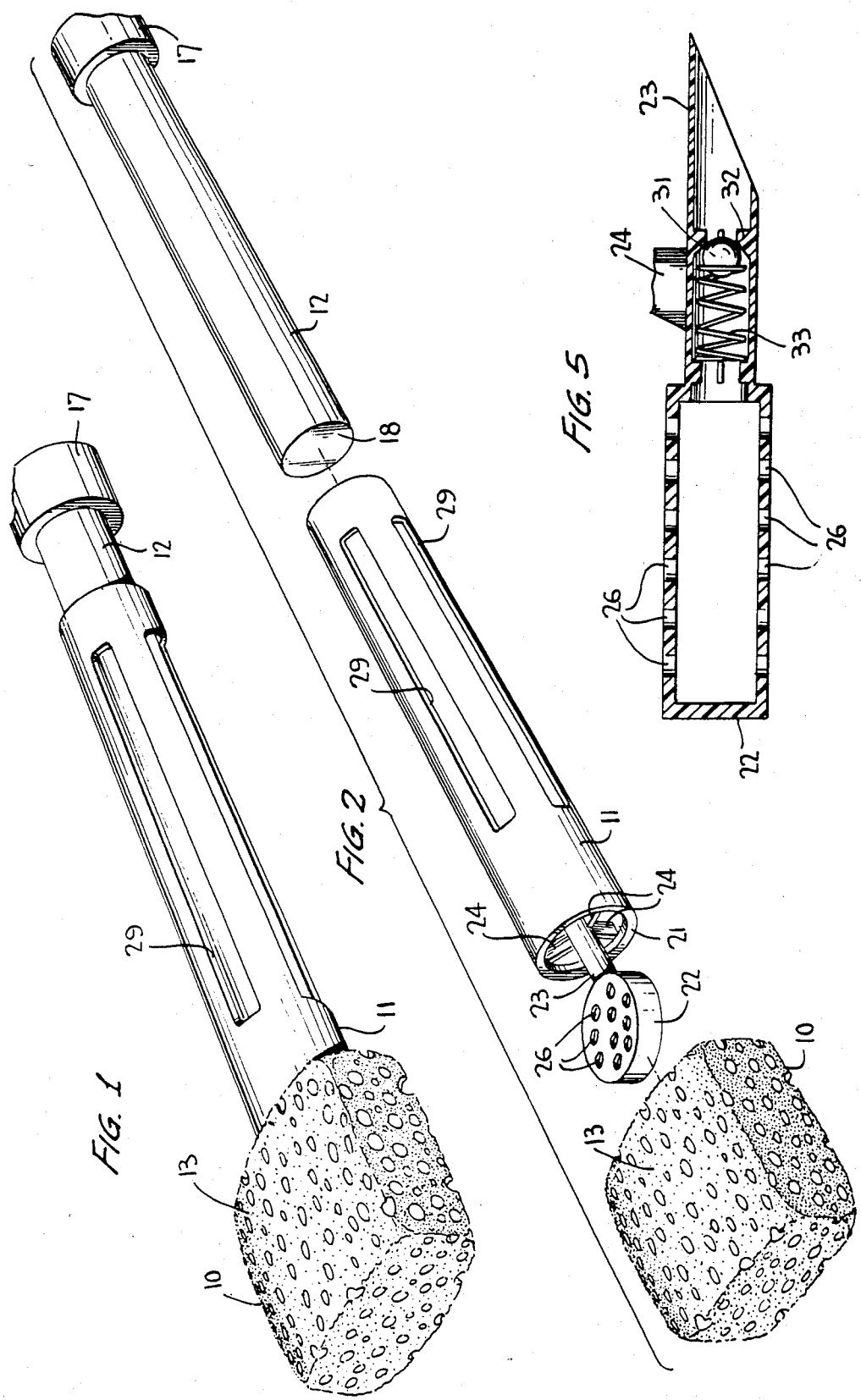

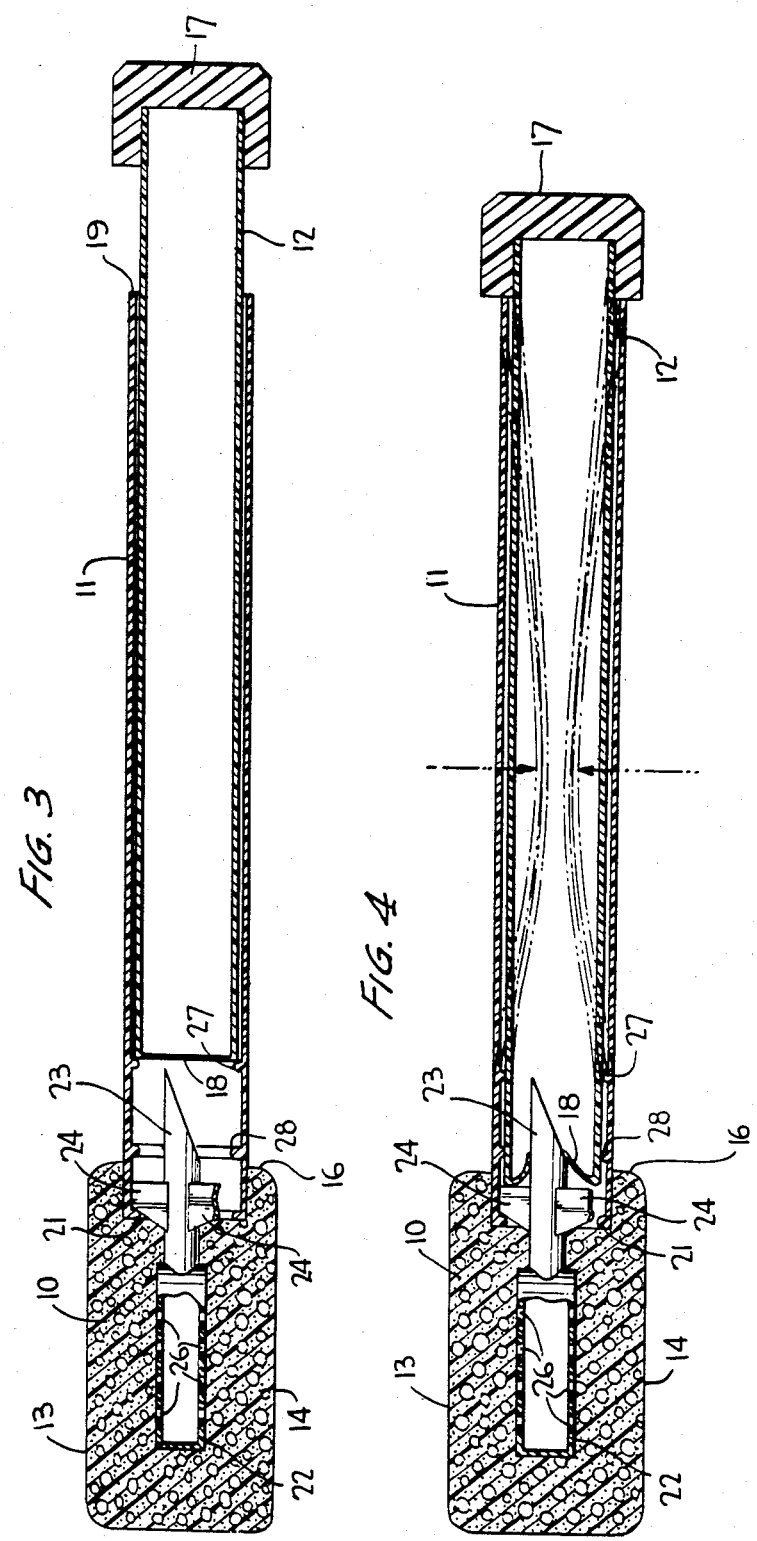

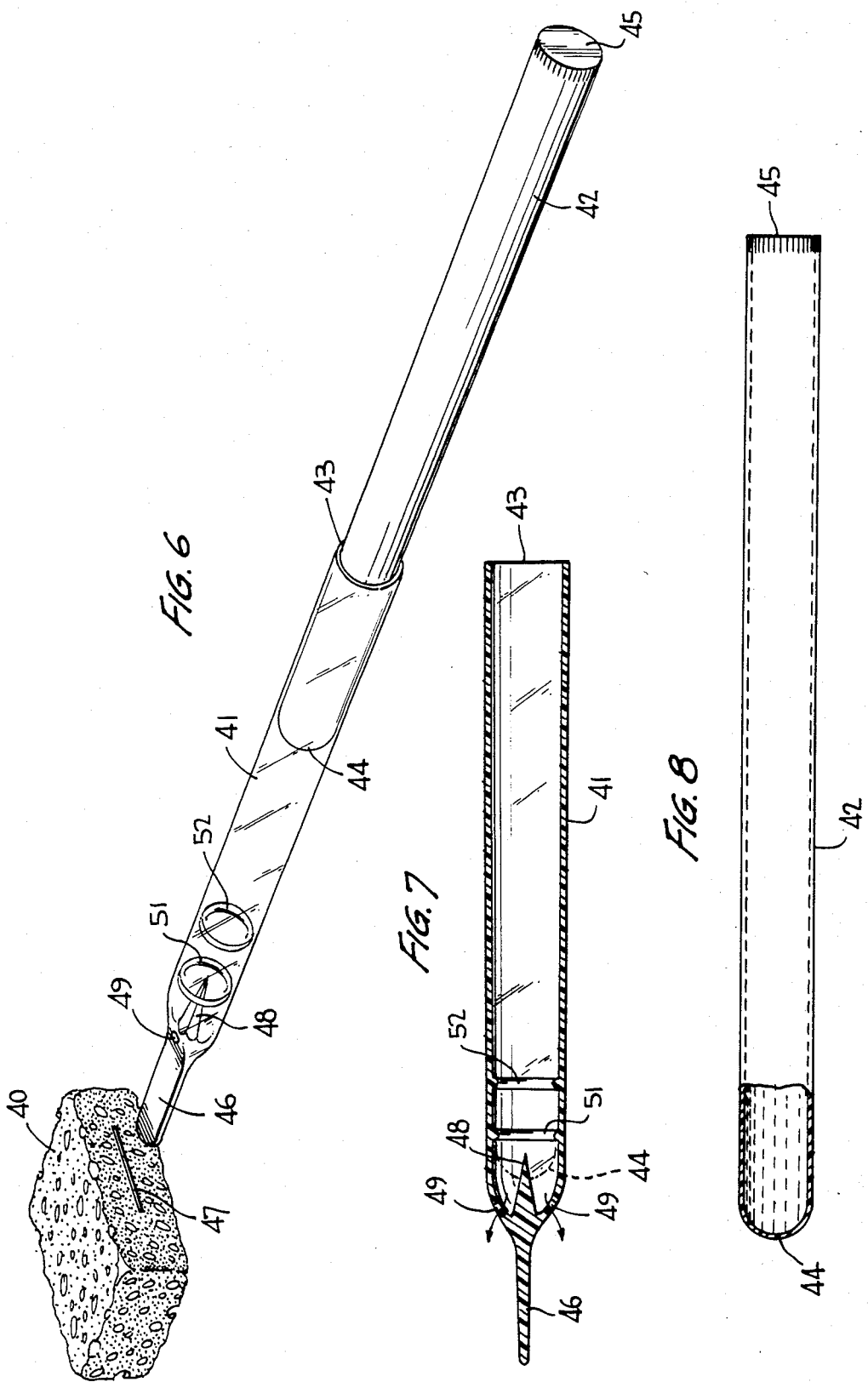

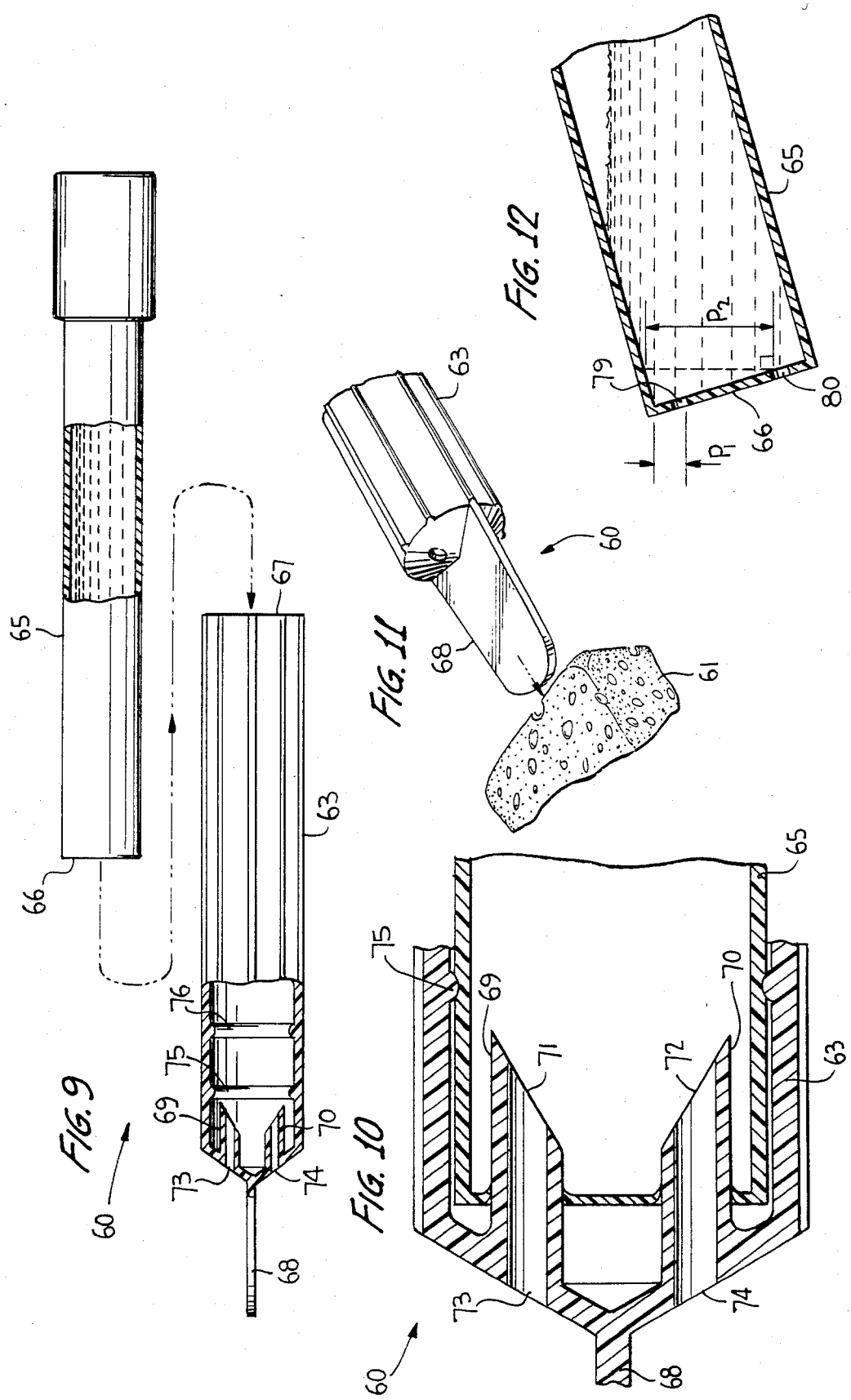

SURGICAL SCRUB

CROSS-REFERENCE TO RELATED APPLICATIONS

This application is our continuation-in-part application of U.S. patent application Ser. No. 241,486, filed Mar. 9, 1981 and entitled "Improved Liquid Dispensing Device", now abandoned and our continuation-in-part of application Ser. No. 298,246, filed Aug. 31, 1981, now U.S. Pat. No. 4,415,288.

TECHNICAL FIELD

The present invention relates generally to liquid dispensers and applicators of the type wherein a premeasured supply of liquid is disposed in an applicator handle and selectively dispensed through the applicator. The invention has particular applicability in the field of aseptic surgery preparation as a preoperative surgical scrub system for use in the operating room.

BACKGROUND OF THE INVENTION

As part of the preparation for many surgical procedures, for example, a surgical operation, it is required that the affected area of the patient be antiseptically cleansed. This requirement has existed for a very long time and the procedures used to meet this requirement have changed dramatically. Originally, jars or cans of gauze sponges or cotton balls were packed, sterilized, and placed in operating rooms. These songes and/or cotton balls were used for scrubbing procedures by holding them with sterile forceps and dipped into a pan containing a soap or antiseptic solution. After the cotton ball or sponge is saturated with the solution, it is wiped on the appropriate area. This procedure was inconvenient for a number of reasons. First, it tended to created a mess due to the open pan and the constant back and forth travel of the sponge or cotton ball between the pan and the patient. Further, the procedure took an undesirably long time and resulted in an inordinate amount of liquid being lost due to splashing, scattering, and waste. Moreover, this procedure tended to use more antiseptic solution than necessary because most medical personnel mistakenly believed that the antiseptic effect was more readily obtained if more solution was used. This is not true and, quite to the contrary, it has been noted that excess solution tends to form pools or puddles under the patient resulting in iodine burn.

Apart from the disadvantage of the forcep and sponge or cotton ball procedure, the lack of standardization of techniques resulted in considerable confusion. Eventually, certain standards did develop. Specifically, the area of the incision on the patient's body must be cleaned thoroughly with a scrub or soap solution for a period between 3 to 10 minutes. Most surgical operations, other than orthopaedic surgery, require 3 minutes of scrubbing time; orthopaedic surgery requires 10 minutes of scrubbing time due to the increased risk of infection. After the scrubbing procedure, the area is dried with a sterile wipe and antiseptic solution is applied. For some procedures, other than orthopaedic surgery, the scrub portion of the precedure is eliminated and only the antiseptic solution is applied. In either case, the standard procedure for applying either the scrub or the antiseptic solution involves starting from the middle of the treated area and proceeding outward in circular or square motions, it being important never to return to a previously treated area with the same surface of the sponge. The sponge may be turned over and the same procedure started once again; that is, as long as a new sponge surface area is used, an already-prepared skin area may be re-contacted. However, one should never apply a used or contaminated sponge surface that has already been in contact with a cleanly prepared skin area.

Attempts to overcome the drawbacks described above in relation to surgical swab and/or scrub apparatus and techniques involve the development of devices in which the liquid to be applied is contained within the device itself, generally in a hollow handle. Examples of such devices may be found in the following U.S. Pat. Nos. 1,221,227; 2,333,070; 3,324,855; 3,508,547; 3,614,245; 3,774,609; 3,847,151; 3,876,314; 3,891,331; 3,896,808; 3,958,571; 4,148,318; and 4,225,254. The devices disclosed in these patents presented considerable improvements over the relatively primitive method of employing individual cotton balls or sponges with forceps and dipping these into the pan of solution as described above. However, many of the devices disclosed in the aforesaid patents are relatively complex to manufacture, thereby resulting in too high a cost for a device which is disposable after a single use. Moreover, many of the devices disclosed in these prior patents have only one available surface for the applicator sponge or swab. For example, the device disclosed in U.S. Pat. No. 4,225,254 provides a generally conical shaped sponge, thereby making it difficult to assure that the same surface area of the sponge does not contact an already treated area of the patient's skin. Moreover, the conical configuration minimizes the available surface area of the sponge. As noted, available clean, unused surface area of the preparation sponge is one of the most important factors governing the pre-surgical preparation technique.

The device disclosed in U.S. Pat. No. 3,847,151 had considerable promise toward solving most of the problems referred to above. That patent discloses a surgical scrub device wherein a sponge applicator is mounted on a nozzle which extends from a hollow handle containing antiseptic solution. The nozzle includes a joint which can be selectively ruptured prior to use so as to permit the solution to flow from the nozzle into the sponge. In practice, however, this device proved to have functional problems. Mass production techniques being what they are, the stress break at the rupturable joint in the nozzle was not always complete and fluid was not always available. In addition, the rupture was not always properly completed by the user of the device, again resulting in a situation where fluid was not available for use. An additional problem with this device is that the scrub solution (soap) tends to fill the sponge too slowly, whereas the swab solution (antiseptic) tends to fill the sponge too quickly. In general, the product, although well conceived, proved not to be reliable in use.

It has been suggested (see U.S. Pat. No. 3,481,676 to Schwartzman) that a liquid applicator can take the form of a cylindrical rupturable liquid-filled cartridge disposd in a tube-like handle having a sharp-edged flow passage disposed therein. The cartridge can be forced against the sharp edge to rupture the cartridge and extend the flow passage through the rupture. This permits the liquid to flow from the cartridge, through the passage, to an applicator which surrounds the passage.

This approach disclosed by Schwartzman is valid for many applicators where a slow rate of fluid application can be tolerated. More particularly, in order for the liquid to be able to flow from the ruptured cartridge, there must be air admitted into the cartridge to replace the outflowing liquid. In the Schwartzman device, inflowing air and outflowing liquid must flow in opposite directions through the single sharp-edged flow passage. This severely limits the liquid outflow rate. For surgical scrub applications, it is important that the sponge or applicator be quickly saturated so that liquid can be quickly applied to the pre-surgical incision site without delaying the surgical procedure. This problem could be remedied in the Schwartzman applicator by providing the cartridge with a valved or other permanent vent opening, much like is done with the cartridge-type fountain pens. However, such opening would not be a satisfactory solution for surgical scrub applications wherein the administered liquid must be maintained sterile in the cartridge.

SUMMARY OF THE INVENTION

It is therefore an object of the present invention to provide a simple, inexpensive, and disposable surgical scrub device which is capable of administering sterile liquid to an incision site for swabbing or scrubbing that site in pre-surgical procedures. It is a further object of the present invention to provide such a device which is devoid of the disadvantages ennumerated above in the devices of the aforementioned patents. It is another object of the present invention to provide such a device useful as a swab or a scrub depending upon the selection of a replacement cartridge of the liquid to be applied. It is a particular object of the present invention to provide a surgical swab or scrub device of the type wherein liquid to be applied is contained within the handle and wherein the liquid can be reliably and quickly applied to the applicator sponge.

In accordance with the preferred embodiment of the present invention, an elongated tubular handle has an applicator sponge permanently or removably secured to one end thereof and accepts the cylindrical cartridge of liquid to its other end. The sponge has two opposite applicator sides. Two rigid hollow spikes are transversely spaced inside the one handle end and point toward the other end so as to be in a position to rupture a forward end of the cartridge when the cartridge is fully inserted into the handle. The spikes are positioned such that one or the other is always vertically higher when the applicator surfaces of the sponge are substantially horizontal. This difference in height reflects itself as a difference in liquid pressure at the punctures in the cartridge, whereby vent air can freely enter the cartridge through the lower pressurized upper puncture, thereby permitting liquid to freely egress through the lower puncture. The spikes are formed as bias or diagonal cuts which reside in respective bias planes that converge toward the said one end of the handle. This increases the spacing between the two punctures and thereby increases the liquid pressure difference at the punctures, this being relative to the spacing and pressure resulting from bias planes which converge toward the other end of the handle.

BRIEF DESCRIPTION OF THE DRAWINGS

The invention will be more fully understood, while still further objects and advantages will become apparent, in the following detailed description of embodiments thereof illustrated in the accompanying drawings, wherein:

FIG. 1 is a view in perspective of the liquid dispensing device constructed in accordance with some of the principles of the present invention;

FIG. 2 is an exploded view in perspective of the device of FIG. 1;

FIG. 3 is a view in longitudinal section of the device of FIG. 1 showing the device in its storage or pre-dispensing condition;

FIG. 4 is a view section similar to that of FIG. 3 but showing the device in its dispensing mode;

FIG. 5 is a detailed view in section of a portion of the device of FIGS. 1-4 illustrating a check valve employed therein;

FIG. 6 is a view in perspective of another embodiment of the present invention;

FIG. 7 is a view in section of the handle member of the embodiment of FIG. 6;

FIG. 8 is a side view in partial section of the cartridge member of the embodiment of FIG. 6;

FIG. 9 is a diagrammatically-exploded view in partial longitudinal section of the preferred embodiment of the present invention;

FIG. 10 is an enlarged detailed view in section of one end of the handle member and cartridge of the embodiment of FIG. 9, showing the manner in which the hollow spikes rupture the liquid-containing cartridge;

FIG. 11 is a view in perspective of a portion of the embodiment of FIG. 9, showing the engagement between the handle member and the applicator sponge; and FIG. 12 is a diagrammatic illustration of the cartridge in the embodiment of FIG. 9 showing the pressure conditions established by rupture of the cartridge which effect free flow of the contained liquid.

DESCRIPTION OF THE PREFERRED EMBODIMENT

Referring to FIGS. 1-5 of the drawings in greater detail, a surgical scrub according to one embodiment of the present invention comprises three (3) major parts, namely: a sponge applicator 10; a tubular handle 11; and a cartridge 12. The sponge 10 may be made from a variety of medically accepted sponge-like materials having a wide density range and coarse or fine textures. Coarse texture may be employed for scrubbing because it is more abrasive; the finer texture may be utilized for application of antiseptic solution. For general use, sponge 10 is ideally two (2) inches square by one (1) inch thick; however, these dimensions are provided by way of example only and size is by no means a limiting factor on the present invention. The sponge is preferably configured to have two (2) large, flate and opposite application surfaces 13 and 14, but again the configuration is not to be considered limiting on the scope of the present invention. Surfaces 13 and 14 may be generally rectangular, as shown, or may be circular, oval, triangular, etc. Sponge 10 is adapted to receive one end of tubular handle 11 through a suitably provided opening in an end surface 16 of the sponge which resides generally perpendicular to the application surfaces 13 and 14. The end surface 16 of sponge 10 may be suitably die-cut in order to receive the end of handle member 11 in the manner described below. For example, sponge 10 may be cut into 2"×4"×½" pieces which are folded in half and glued on portions of the inner surface to cover the received portion of handle 11. Alternatively, sponge 10 may be die-cut into a piece 2"×2" and slotted at surface 13 to permit insertion of the handle member 11. Adhesive may be employed to stabilize the sponge onto the handle member.

Cartridge member 12 is a generally tubular member whose outside periphery matches the inside periphery of a portion of tubular handle 11. The outside dimensions of cartridge 12 substantially match the inside dimensions of tubular handle 11 so that the cartridge can freely slide longitudinally within the handle member. The overall size can range from as little as a 5 ml capacity to as large as a 240ml capacity. In this regard, the entire unit can be selected to be of the appropriate size for the desired amount of liquid to be administered. For a sponge 10 having dimensions of 2"×2"×1", the average capacity of the cartridge would be 30 ml. Cartridge 12 may be produced on a form, fill and seal machine in a continuous operation. Under such circumstances, the container is blow molded, filled with the desired fluid, and sealed in continuous steps of one overall operation. The configuration of the cartridge should not be considered limited and may be fabricated by any plastic-forming equipment, as long as the resulting product has the overall density required to contain the liquid employed. The tubular cartridge should have a plastic density which permits simple placement into the tubular handle while providing sufficient rigidity to permit sliding movement through the handle. The cap 17 for cartridge 12 is disposed at one end thereof and may be formed integrally with the cartridge, if desired. The opposite end 18 of the cartridge may be of the same density as the overall cartridge but in any event, must be suitable to permit rupture and penetration of the cartridge in the manner described herein below.

In this respect, the forward end 18 of the cartridge is preferably thinner than the cap 17 which should be considerably heavier to afford a more rigid plastic form and thereby facilitate application of a pushing force required to displace cartridge 12 with the handle 11 so that forward end 18 can be ruptured.

Handle member 11 comprises, for the most part, a rigid plastic tube having an open end 19 adapted to receive cartridge 12 therein when the cartridge is inserted with its forward end 18 first. The opposite end 21 of handle 11 extends partway into sponge 10 and includes, preferably formed as an integral part thereof, a dispensing chamber 22. The dispensing chamber projects forwardly of tube 21 into sponge 10. A tubular spike 23 extends rearwardly from the dispensing chamber 22 into the tubular portion of handle 11 and is provided with a plurality of radially-extending stabilizing fins 24 which fixedly engage the interior surface of the tubular handle member 11. As noted above, it is preferable that the dispensing chamber 22, spike 23, and stabilizing fins 24 be formed integrally with tubular section 11 by means of an appropriate plastic-forming technique; alternatively, these components may form a part of a separate unit which is secured at the remote ends of stabilizing fins 24 to the interior wall of tubular member 11 by means of a suitable adhesive material or the like. For the latter configuration, annular lip is formed, as shown, at the forward end 21 of tubular handle member 11 to retain the fins 24 in proper position.

Dispensing chamber 22 may take the form of a shallow cylinder, as shown, or any other suitable configuration. In the preferred shallow cylindrical configuration shown, the opposite circular ends of the chambers are provided with a plurality of apertures 26 which provide fluid communication between the interior of chamber 22 and the surrounding interior of sponge 10. The primary function of dispensing chamber 22 is to provide free flow of pressurized fluid therein into the sponge to soak the sponge for application to the appropriate body surface area. A secondary function of dispensing chamber 22 is to provide sufficient rigidity to the sponge during application of the liquid from the sponge to the patient's body. This latter function is best served when the apertured ends of dispensing chamber 22 have the largest possible surface area. However, smaller dispensing chmabers can be utilized with effective results.

Spike 23 is in the form of a tube which projects rearwardly from dispensing chamber 22 and has its interior in flow communication therewith. The end of spike 23 remote from chamber 22 is cut along a bias to taper to a fine point, much like a conventional intravenous spike used to puncture IV bags.

A narrow annular shoulder 27 projects radially inward from the interior wall of tubular handle 11 at an axial location just beyond the tip of spike 23. More specifically, the tip of spike 23 is spaced a slightly shorter distance from end 21 of tubular handle 11 than is the annular lip 27. Lip 27 serves as a flexible stop for end 18 of cartridge 12. Specifically, as illustrated in FIG. 3, the outer edges of the forward end 18 of cartridge 12 about lip 27 in the stand-by condition of the unit. Lip 27 thereby spaces the forward end 18 of the cartridge from the point of spike 23. When it is desired to apply fluid from the cartridge to a surface area of the patient, or the like, cartridge 12 is pushed forward within tube 11, causing lip 27 to flex and permitting the forward end 18 of cartridge 12 to move forwardly and be ruptured by the point of spike 23. This is best illustrated in FIG. 4. The hollow spine 23 enters the cartridge via the cartridge end 18 and permits liquid from the cartridge to flow through the spike to the dispensing chamber 22 where it flows through apertures 26 to soak the sponge 10. A sealing ring, for example, an O-ring 28, projects from the interior surface of handle member 11 radially inward at an axial location between end 21 and stop lip 27. The sealing ring 28 prevents fluid from the sponge from flowing back past sealing member 28 into handle 11.

Tubular handle 11 is provided with a plurality of longitudinally-extending cut-out slots 29. These slots are provided to permit radial compression of the handle 11 so that cartridge 12 may be compressed and liquid forced therefrom into the sponge. It will be appreciated that this compression can be readily achieved by grasping handle 11 in the palm of one's hand and squeezing the hand closed. Alternatively, liquid feed from cartridge 12 to sponge 10 may be effected by gravity flow by simply holding the unit with end 17 upward.

In some applications, it may be desirable to prevent back-flow of dispensed liquid from the sponge and/or dispensing chamber 22 to the cartridge 12. In such cases, a check valve may be supplied within the hollow spike 23 as illustrated in FIG. 5. Specifically, a ball member 31 is disposed within the hollow spike 23 and is biased rearwardly toward the sharp spike end by means of a spring 33. The rearwardly biased ball member 31 sits in a valve seat 32 in the non-operating position of the unit to block flow through the hollow spike. If fluid in the cartridge 12 is pressurized, such as by compressing the handle 11, ball member 31 is unseated from seat 32 by the pressurized liquid which is then permitted to flow into the dispensing chamber 22. When the pressure of the liquid in cartridge 12, as would be necessary to result in a reversed flow of the liquid, spring 33 forces ball member 31 to its closed position to preclude reverse flow.

Referring now to FIGS. 6–8 of the accompanying drawings, a second embodiment of the dispenser of the present invention is illustrated. In this embodiment, the primary difference from the embodiment described above relates to the forward or sponge-end of the handle member and the manner in which the sponge is supported and dispensed liquid flows to the sponge. Specifically, a second embodiment includes a sponge applicator 40, a hollow tubular handle 41 and a cartridge 42 which is slidably received by handle 41 through open rearward end 43 of the handle. Sponge 40 is similar in function and configuration to sponge 10 of the embodiment illustrated in FIGS. 1–5 and partakes of all of the design features and considerations set forth above for sponge 10. Likewise, cartridge 42 is functionally and structurally similar to cartridge 12 illustrated and described in relation to the embodiment of FIGS. 1–5. In the embodiment of FIGS. 6–8, the forward end 44 of 42 is rounded and readily susceptible to puncture by a spike in the manner described below. The rearward end 45 of cartridge 42 is more rigid to facilitate insertion of cartridge 42 into handle 41 by pushing the rearward end 45 appropriately.

Handle member 41 is similar in function to handle 11 in the embodiments of FIGS. 1–5. As noted above, the rearward end 43 of handle 41 is open to receive the forward end of cartridge 42. The forward end of handle 41 tapers to form a paddle-shaped or duck-billed shaped member 46 which projects forwardly of handle member 41. This paddle-shaped projection 46 is adapted to be received in a suitably provided slot 47 in sponge 40. Projection 46 thus serves to support sponge 40 into which it projects. For this purpose, projection 46 is made somewhat flexible to permit relative flexure between the sponge 40 and handle member 41. A conical spike 48 projects rearwardly of projection 46 into the interior of the forward end of handle 41. Spike 48 serves the purpose of rupturing the forward end 44 of cartridge 42 when that cartridge is sufficiently inserted into handle member 41. To this end, although spike 48 is shown as a sharp, conical projection, it may take other forms, such as "bullet-nosed" configuration. The important point is that the rearward most part of spike 48 should be sufficiently sharp to permit it to rupture forward end 44 of the cartridge. Spike 48 differs from spike 23 in the embodiment of FIGS. 1–5 in that it does not provide an internal flow path whereby fluid from cartridge 42 can flow out of handle 41; in other words, spike 48 is not hollow. Instead, the forward end of handle 41, rearwardly of projection 46, is provided with a plurality of apertures 49 through which liquid can escape from the interior of handle 41 after it has been squeezed from the ruptured cartridge 42. Apertures 49 are disposed at a longitudinal position of handle 41 which is inserted within slots 47 of sponge 40 so that all of the liquid which escapes from apertures 49 is absorbed into sponge 40.

A narrow annular shoulder 51 projects radially inward from the interior wall of tubular handle 41 at an axial location just rearward of the rearward extremity of spike 48. A similar annular shoulder 52 projects radially inward from the interior wall of handle 41 at a location spaced slightly rearward of shoulder 51. Shoulder 52 serves as a stop for forward end 44 of cartridge 52 when the cartridge is inserted in handle 41. To this end, the axial position of shoulder 52 is such that when it stops further insertion of the cartridge into handle 41, the forward end 44 of the cartridge is spaced from the rearward extremity of spike 48. In the manner similar to that described above in relation to the embodiment of FIGS. 1–5, cartridge 42 can be forced beyond the stop shoulder 52 so that the forward end 44 of the cartridge 42 can be punctured by spike 48. Shoulder 51 serves as a fluid seal, in conjunction with the peripheral wall of the ruptured cartridge 42, to prevent the fluid from flowing rearwardly in the handle member 41. Handle member 41 may be provided with longitudinally-extending cut-out slots, such as slots 29 in handle member 11, to facilitate radial compression of handle member 41 and thereby force liquid from cartridge 43 through apertures 49 into sponge 40.

In a typical, but by no means limiting configuration of the embodiment of FIGS. 6–8, the various parts have the dimensions noted below. Cartridge 42 is 8 inches long and has a $\frac{5}{8}$ inch diameter. Sponge 40 has top and bottom surfaces which are $1\frac{3}{4}"$ square and $\frac{7}{8}"$ deep. The overall length of handle member 41 is $6\frac{7}{8}"$, the paddle-shaped projection 46 being 1" long. The inner diameter of handle 41 is $\frac{5}{8}"$ and the thickness of the walls of handle 41 is approximately 0.050". The length of spike 48 is approximately $\frac{3}{8}"$. The tubular handle 41 may, if desired, have a taper on the order of 0.5° from rearward end 43 toward paddle 46 in order to facilitate insertion of cartridge 42 and eventual retention of the cartridge in the handle. The projection 46 is preferably as thin as possible to enhance flexibility and the end of the projection is preferably rounded rather than squared-off. The size of apertures 49 depends upon the desired flow characteristics for the device in view of the liquid being dispensed.

A surgical scrub device 60, constituting the preferred embodiment of the present invention, is illustrated in FIGS. 9, 10 and 11, to which specific reference is now made. Surgical scrub unit 60 is made of three (3) separate parts, namely a sponge applicator 61, a tubular handle 63, and a liquid-containing cartridge 65. The sponge applicator 61 is the same type of applicator which is described above for sponge applicators 10 and 40 and partakes of all of the desired features and considerations set forth above for those sponge applicators. Likewise, cartridge 65 is functionally and structurally similar to cartridges 12 and 42 and partakes of the same design features and considerations for the cartridges set forth above.

Handle member 63 is a rigid plastic hollow tube having an open rearward end 67 adapted to receive cartridge 65 therein when the forward end 66 of the cartridge 65 is inserted first into the handle. The opposite or forward end of handle 63 terminates in a paddle-shaped projection 68 which is adapted to be received in a suitably provided slot in sponge applicator 61. In this manner, the paddle 68 serves to support the sponge and permits compression of a sponge applicator surface against a pre-surgical incision site by tilting the paddle end of the handle downward against the site. For this purpose, the paddle 68 is made somewhat flexible transversely of the longitudinal dimension of the handle in order to permit flexure of the sponge relative to the handle.

The interior surface of the forward end of handle 63 is concave and has a pair of radially or transversely spaced hollow spikes 69, 70 projecting therefrom toward the open rearward end 67 of the handle. Spikes 69 and 70 are respective tubular projections which are cut along respective bias planes 71, 72 which converge toward one another in a direction toward the paddle 68. This orientation of the spike-forming bias plane provides the greater possible transverse spacing between the pointed ends of the spikes. This feature, as described in detail below, increases the free flow of liquid from the punctured cartridge 65. The hollow interiors of spikes 69, 70 communicate with respective openings 73, 74 in the forward end of handle 63. Importantly, the spikes 69 and 70, and their respective openings 73, 74 are disposed on opposite transverse sides of paddle 68. Preferably, the longitudinal center lines of the hollow spikes 69 and 70 reside in a plane which perpendicularly bisects the paddle 68 so that the spikes are centered relative to the transverse dimension of the paddle. The goal, in any event, is to maximize the spacing between the cartridge punctures made by the spikes 69 and 70, and to assure that one spike is always higher than the other when the applicator surface of the sponge is oriented substantially horizontally.

A narrow annular shoulder 75 projects radially inward from the interior wall of tube handle 60 at an axial location just rearward of the rearward extremities of spikes 69 and 70. A similar annular shoulder 76 projects radially inward from the interior wall of handle 63 at a location spaced slightly rearward of shoulder 75. Shoulder 76 serves as a stop for the forward end 66 of the cartridge 65 when the cartridge is inserted into the handle 63. To this end, the axial position of shoulder 76 is such that it when it stops further insertion of the cartridge to the handle 63, the forward end 66 of the cartridge is spaced from the rearward extremity of spikes 69, 70. In the manner similar to that described above in relation to the embodiments of FIGS. 1–5 and FIGS. 6–8, cartridge 65 can be forced beyond the stop shoulder 76 so that the forward end 66 of the cartridge can be punctured by the spikes. Shoulder 75 serves as a fluid seal, in conjunction with the peripheral wall of ruptured cartridge 65, to prevent the fluid from the ruptured cartridge from flowing rearwardly in the handle member 63. Handle member 63 may be provided with longitudinally-extending cut-out slots, such as slots 29 in handle member 11, to facilitate radial compression of the handle member and thereby force liquid from the cartridge into the sponge.

The manner in which the embodiment of FIGS. 9–11 provides free out-flow from the cartridge to the sponge can best be explained with the aid of the diagrammatic illustration of cartridge 65 presented in FIG. 12. The forward end 66 of the cartridge is shown with two (2) punctures 79 and 80 which are assumed to have been made by spikes 69 and 70, respectively. The spikes have been omitted from the illustration of FIG. 12 for purposes of retaining clarity. The cartridge 65 is shown with its forward end tipped slightly downward from horizontal, as would be the case when the unit is in use. Since the sponge applicator surfaces are substantially horizontal in use, the paddle 68 is tilted slightly downward from horizontal and flexed back toward horizontal against the pre-surgical site. Therefore, puncture 79 will be disposed at a higher level than the puncture 80. It should be noted that, if the handle is rotated 180° about its central longitudinal axis, so that the sponge applicator surfaces are reversed in position, puncture 80 will be disposed at a higher level than puncture 79 and the same advantageous free flow operation will ensue.

In either case, the liquid pressure head at the higher level puncture (79 in the present example) is relatively small and is designated $P_1$ in FIG. 12. This pressure is determined by the vertical height of liquid subsisting in the cartridge above puncture 79. The pressure head 72 at the lower puncture 80 is designated $P_2$ and is determined by the vertical height of the liquid subsisting above puncture 80 in the cartridge. Since puncture 80 is considerably lower in the cartridge than puncture 79, the pressure $P_2$ is considerably greater than the pressure $P_1$. If the pressure $P_1$ is sufficiently low relative to atmospheric pressure, air enters puncture 79 via handle opening 73 at hollow spike 69, and liquid flows out through puncture 80, spike 70, and handle opening 74 to sponge 61. As the handle and cartridge are tilted more and more toward vertical (counterclockwise in FIG. 12), the vertical column of liquid above upper puncture 79 increases in height, thereby increasing the liquid pressure $P_1$ at puncture 79. At some position of the cartridge, the liquid pressure $P_1$ is sufficiently greater than atmospheric pressure so that air does not readily enter the cartridge via puncture 79. However, the normal orientation of the surgical scrub, in use, is with its forward end tilted just slightly downward from horizontal, at which position the pressure $P_1$ is close to a minimum and, in any event, less than atmospheric pressure.

It wil be appreciated that the greater the spacing between punctures 79 and 80, the greater will be the pressure differential caused by the liquid in the cartridge. Further, it is important that the punctures 79 and 80 be as close to the rims of forward edge 66 of the cartridge as possible so that the pressure $P_1$ can be made as low as possible relative to ambient pressure. More specifically, when the punctures are very close to the rim of the forward end 66 of cartridge 65, the height of liquid in the cartridge above the puncture, which height produces the pressure $P_1$, is minimized for any orientation of the cartridge.

In a typical, but by no means limiting, configuration of the preferred embodiment of FIGS. 9–11, the various parts have the following dimensions. Cartridge 65 is 6 inches long and has a 0.652 inch diameter. Sponge 61 has top and bottom surfaces which are 1¾ inches square and is ⅜ inch deep. The overall length of handle member 63 is 5.512 inches, the paddle-shaped projection 68 being 1 inch long. The inner diameter of handle 63 is 0.687 inches and the thickness of the walls of handle 63 is approximately 0.069 inches. The length of the spike 48 is approximately ⅜ inch. Each spike 69, 70 has an inner diameter of 0.114 inches and an outer diameter of 0.184 inches. The spike-forming bias cut is made at a 30° angle from the longitudinal axis of the handle so that planes 71, 72 converge at a 60° angle. The rearwardmost point of the tips of spikes 69 and 70 are 3.906 inches from open handle end 67. The paddle 68 is preferably as thin as possible to enhance flexibility, and the end of the projection is preferably rounded rather than squared off. The unit as described is simple and inexpensive to fabricate and is therefore readily disposable after a single use. Specifically, the unit, in the optimal case, may be fabricated from only three (3) separate components, namely, the sponge, the cartridge, and the tubular handle. The cartridges, of course, may be interchangeable so that a variety of different liquids may be employed during the same procedure, if an insufficient amount of liquid has been applied. The cartridges are easy to change and remain sterile until used. The user of the device need not wear a surgical glove in view of the sterility of the cartridge arrangement shown. The unit may be simply activated by merely grasping the handle in one hand and gently wrapping the end of the cartridge on a hard surface so as to force the forward end of the cartridge against the spikes. Actuation is thus reliable and easily effected and the liquid to be dispensed flows freely to the sponge.

While we have described and illustrated specific embodiments of our invention, it will be clear that variations of the details of construction which are specifically illustrated and described, may be resorted to without departing from the true spirit and scope of the invention as defined in the appended claims.

What is claimed is:

1. A surgical scrub device comprising:
   an elongated hollow handle member having first and second longitudinally-spaced ends, said first end being open;
   an absorbent sponge-like member disposed about said second end of said handle member;
   an elongated fluid-containing cartridge adapted for longitudinal slidability in said handle member, said cartridge having a rupturable forward end by which it is inserted into said open first end of said handle member; and
   first and second transvesely spaced hollow spikes formed as part of and inside said handle member proximate said second end, each spike having a pointed end projecting longitudinally toward said first end, each hollow spike providing flow communication between the interior of said handle member and respective locations within said sponge-like member through said second end of said handle member;
   wherein said spikes are positioned to provide two transversely-spaced punctures in said forward end of said cartridge in response to a predetermined slidable insertion of said cartridge in said handle member;
   whereby each of said hollow spikes, when disposed vertically lower than the other hollow spike, serves to conduct fluid out from said handle member interior to said sponge-like member while the other hollow spike conducts vent air into the hollow member interior.

2. The surgical scrub device according to claim 1, wherein said second end of said handle member is in the form of a transversely flexibe paddle, and wherein said sponge-like member has a slit defined therein to recieve said flexible paddle, thereby to engage said handle member.

3. The surgical scrub device according to claim 2, wherein said sponge-like member has first and second opposite application surfaces, wherein said paddle has first and second opposite flat surfaces and wherein said first and second hollow spikes provide flow communication from the interior of said handle member to locations along said first and second flat surfaces, respectively of said paddle.

4. The surgical scrub device according to claim 3, wherein said first and second spikes are hollow tubes which are cut along respective first and second bias planes to define said pointed ends.

5. The surgical scrub device aaccording to claim 4, wherein the largest transverse spacing between portions of said hollow spikes is at said pointed ends.

6. The surgical scrub device according to claim 4, wherein said first and second bias planes converge in a direction toward said second end of said handle member.

7. The surgical scrub device according to claim 6, wherein the hollow interior of said handle member is cylindrical and has a central longitudinal axis, wherein said first and second hollow spikes are transversely spaced symmetrically with respect to said central longitudinal axis, there being a further plane which bisects both spikes and perpendicularly bisects said first and second opposite flat surfaces of said paddle.

8. The surgical scrub device according to claim 7, wherein said hollow handle member includes a generally cylindrical interior surface along which said cartridge is longitudinally slidable and further comprises an annular stop member projecting radially inward therefrom for resiliently engaging said forward end of said cartridge member at a location wherein the cartridge member is spaced slightly longitudinally from said projecting pointed ends of said spikes, the resilient engagement of said forward cartridge end by said annular stop member being such as to be overcome by force exerted longitudinally on said cartridge toward said projecting pointed ends to permit passage of said forward end of said cartridge member into rupturable engagement with said spikes.

9. The surgical scrub device according to claim 8, wherein said hollow handle member is provided with a plurality of longitudinally-extending slots for sufficiently weakening the compressive strength of said handle member to permit compression thereof to compress said cartridge.

10. The surgical scrub device according to claim 1, wherein said second end of said handle member comprises a generally paddle-shaped member projecting axially outward from said second end and adapted to be received and engaged by said sponge-like member.

11. The surgical scrub device according to claim 10, wherein said first and second spikes are hollow tubes which are cut along respective first and second bias planes to define said pointed ends.

12. The surgical scrub device accoding to claim 11, wherein said first and second bias planes converge in a direction toward said second end of said handle member.

13. The surgical scrub device according to claim 12, wherein the hollow interior of said handle member is cylindrical and has a central longitudinal axis, wherein said first and second hollow spikes are transversely spaced symmetrically with respect to said central longitudinal axis, there being a further plane which bisects both spikes and perpendicularly bisects said paddle.

14. The surgical scrub device according to claim 1, wherein said first and second spikes are hollow tubes which are cut along respective first and second bias planes to define said pointed ends.

15. The surgical scrub device according to claim 14, wherein said first and second bias planes converge in a direction toward said second end of said handle member.

16. The surgical scrub device according to claim 1, wherein said sponge-like member includes first and second opposite application surfaces and a further surface oriented generally perpendicular to said application surfaces and through which said second end of said handle member extends, said application surfaces having substantially larger surface areas than the surface area of said further surface.

* * * * *